United States Patent [19]

Runkis

[11] Patent Number: 5,143,536
[45] Date of Patent: Sep. 1, 1992

[54] GEL ROOTING COMPOSITION AND METHOD

[76] Inventor: Walter H. Runkis, 457 Oak Manor, Fairfax, Calif. 94930

[21] Appl. No.: 104,788

[22] Filed: Oct. 5, 1987

[51] Int. Cl.$^5$ ............................................. A01N 25/04
[52] U.S. Cl. ............................................. 71/77; 71/96; 71/114; 71/116; 71/123; 71/DIG. 1; 548/469; 548/494
[58] Field of Search ............... 71/77, DIG. 1, 96, 114, 71/116, 123

[56] References Cited

U.S. PATENT DOCUMENTS

| | | | |
|---|---|---|---|
| 3,876,761 | 4/1975 | Shepherd | 424/78 |
| 4,071,508 | 1/1978 | Steckler | 260/79.3 |
| 4,177,056 | 12/1979 | Mueller et al. | 71/93 |
| 4,227,911 | 10/1980 | Leonard et al. | 71/77 |

OTHER PUBLICATIONS

Smith et al. Chem. Abst. vol. 78 (1973) 132707f.

*Primary Examiner*—Carolyn Elmore
*Assistant Examiner*—B. M. Burn
*Attorney, Agent, or Firm*—Fliesler, Dubb, Meyer & Lovejoy

[57] ABSTRACT

A rooting composition is set forth comprising a water swellable gel containing auxin in an amount effective to stimulate root growth, the gel comprising a high molecular weight organic acid, ketone or ester or combinations thereof. Root formation of a cutting is stimulated by planting the cutting in the soil with the aforementioned rooting composition adhered to the portion of the cutting proximal where it was cut from a living plant. The auxins are maintained close to the cutting whereby they are highly effective and the gel serves as an artificial root to bring water and nutrients to the cutting as it develops its own root system.

24 Claims, No Drawings

GEL ROOTING COMPOSITION AND METHOD

TECHNICAL FIELD

The invention relates to a gel rooting composition including auxins and to a method of stimulating root formation utilizing such a composition.

BACKGROUND ART

The use of auxins to promote root formation is well known. Usually the auxins are applied by wetting a cutting and dipping it in a powdered auxin formulation. Or, the auxin can be dissolved in an organic solvent, sprayed onto the cutting, sometimes in the presence of a resin, and the organic solvent evaporated away.

Several problems exist with such auxin compositions as are discussed above and with the known methods for applying such auxin compositions. Auxins are very slightly soluble in water. Accordingly, only a small portion dissolves and is absorbed by the plant per given unit of time. Yet, during watering, the auxins of the prior art can be readily washed away from the cutting due to the dual physical actions of flowing water and a very small solubility constant. As a result, much of the auxin is washed into the soil and is not absorbed by the cutting where it can serve its root growth stimulating function.

Even when the prior art auxin compositions are not washed away and the auxins serve their root growth stimulating function, the new roots develop only sparsely and slowly per unit period of time and therefore very few roots supply the nutrients which support the initial growth of the cutting. This leads to a relatively slow start for plant growth, as well as increasing that period where cuttings are extremely sensitive to soil diseases such as pythium and phytophthora.

The present invention is directed to overcoming one or more of the problems as set forth above.

DISCLOSURE OF INVENTION

In accordance with the present invention a rooting composition is set forth comprising a water swellable gel containing one or more auxins in an amount effective to stimulate root growth, the gel comprising a high molecular weight organic acid, ketone, ester or a combination thereof.

In accordance with another embodiment of the present invention a method of stimulating root formation of a cutting is set forth comprising adhering a water swellable gel as set forth above to the portion of the cutting proximal where it was cut from a living plant and planting the cutting with the gel adhered thereto in soil or artificial growing medium.

The composition of the present invention has the advantage that auxins are held therein generally by solvation effects and hydrogen bonding to the gel. This prevents or greatly reduces the tendency of the auxin to be washed away to the surrounding soil. Furthermore, the configuration of the auxins in their hydrogen bonded condition are more readily absorbed by the plant cutting. That is, since the gel is swellable it can absorb water and dissolve nutrients and carry them to the cutting via osmotic pressure and chemical potential effects. And, the gel itself acts as an artificial root as the cutting is developing its natural root system. That is, since the gel is swellable it can absorb water and dissolved nutrients and carry them to the cutting. This leads to a significantly faster growth rate for the cutting following its initial planting. It is also somewhat easier to plant the cutting with the gel attached than it is to plant cuttings with prior art powdered compositions attached since the prior art powdered compositions more easily fall off of the cutting during handling.

BEST MODE FOR CARRYING OUT INVENTION

The rooting composition of the present invention comprises as an essential component thereof a water swellable gel comprising a high molecular weight organic acid, ketone or ester or combinations thereof. Such gels may include, for example, polyacrylic acid polymers, including salt forms thereof, carboxyvinyl polymers, pyrrolidone polymers, gels made from diclofenac salts, carboxyvinyl polymers, copolymers of vinyl acetate with polyvinyl ethers, polymers of acrylic acid and acrylic acid esters and acrylic acid derivatives with polyhydroxy compounds having at least 3 and preferably not more than 8 hydroxy groups, such as saccharides, glycerol, and mannitol, sulfonated polyvinyl toluene, copolymers of acrylonitrile, and the like. Particularly useful polymers are polycarboxylate hydrocarbon polymers whose carboxyl groups are amended to form an alkaline metal, ammonium or amine salt. The molecular weight of such polymers range from 30,000 to 4,000,000. The polymer should preferably have neutralization equivalents of from 50 to 500, expressed as grams of dry polymer neutralized by one equivalent of lithium, sodium or potassium hydroxide. Such polymers include the polymethacrylic acids by which is meant the free acids and polymers which are hydrolizable to free acids and which have been hydrolized to a substantial degree. All chemical combinations and derivatives of these materials which cause a water swellable gel in which the auxins, trace elements and synergists are either in solution or in suspension in appropriate concentration so as to be conducive to root formation are usable. Particularly useful polymers are made and sold by the B. F. Goodrich Company under the trademark "Carbopol". The polymer is substantially a polyacrylic acid cross-linked with a polyalkenyl polyether. The B. F. Goodrich Chemical Company sells several of these under different designations, for example, "Carbopol 934" "Carbopol 940" and "Carbopol 941". The cross-linking agent, that is the polyalkenyl polyether, may be, for example, polyallyl sucrose and/or polyallyl pentaerythritol. Such gels will generally be in basic, e.g., ammonium form. However, any polymer which has the same or similar physical and chemical characteristics and properties and to which the auxin can form hydrogen bonds is satisfactory for use in the practice of the invention.

A great number of auxins are known to the art. Esentially any of these can be utilized in practicing the present invention. Such auxins include, for example, indole-3-butyric acid (IBA), 1-naphthalene-acetic acid (NAA), phenyl indole-3-butyrate, phenoxyacetic acid, phenyl indole-3-thiobutyrate, indole-propionic acid, phenylacetic acid, indole cinnamic acid, phenyl-indole-3-acetate, 4-chlorophenyl indole-3-butyrate, 4-chlorophenyl indole-3-acetate, 2,4,6-tribromophenyl indole-3-butyrate, phenyl indole-3-thioloacetate, 2,4-dichlorophenyl indole-3-butyrate, 2,4,6-tri-bromophenyl indole-3-acetate, 4-carboxyphenyl indole-3-acetate, 4-carbethoxyphenyl indole-3-butyrate, 4-(carbomethoxyvinylenephenyl) indole-3-acetate, 4-(carbomethoxyvinylephenyl) indole-3-butyrate, 4-(carbomethoxyvinylene-2,6- dimethoxyphenyl) indole-3-acetate, 4-(carbomethoxyvinylene-2,6-di-methoxyphenyl) indole-3-butyrate, and caulerpin. Mixtures and salts of the above auxins can also be used. For example, mixtures of IBA and NAA are very suitably used. Furthermore, the auxins can be used along with synergists for their action.

The auxin or auxins used, when listed above as an acid, can advantageously be in lithium salt form. This can be accomplished, advantageously, by reacting the acid type auxin(s), e.g., a mixture of IBA and NAA, with sufficient lithium hydroxide, suitably a very small molar excess of lithium hydroxide, to provide a lithium ion for each IBA and NAA molecule. This can be done prior to incorporation of the auxin(s) with the gel or simultaneously. For example, the auxin(s) and an appropriate amount of lithium hydroxide can be combined and then added to ungelled Carbopol solution (the lithium hydroxide will initiate gelling) and the solution can then be more adequately gelled, e.g., by adding an appropriate amount of ammonium hydroxide (which also provides nitrogen nutrient) and mixing. Other nutrients, fungicides and bactericides may also be incorporated at this time.

The auxin, or mixture of auxins, must be present in an amount effective to stimulate root growth. The amount of auxins needed will vary significantly with the auxin used and whether or not a synergist is present. However, the concentration of auxin will generally fall within a range from about 0.1% to about 5%, more preferably from about 0.3% to about 3%, the %s being weight per volume. In accordance with the present invention one can utilize somewhat less auxin per unit volume of solvent than is used in prior art compositions due to increased effectiveness of the auxin since it is kept in the vicinity of the cutting.

The gel may further include nutrients for the cutting. Such nutrients may include, for example, one or more of nitrogen, phosphorous, potassium, calcium, magnesium, boron, chlorine, cobalt, copper, iron, manganese, molybdenum, sodium, zinc and sulfur, in elemental or appropriate molecular forms compatible with solvation in the gel.

The physical-chemical properties of the gel cause increased solvation of some of the ionic complexes and forms of these substances. In addition, insoluble nutrients can be held in suspension. Both of these effects increase the amount of these nutrients, synergists and auxins available to the root generation chemistry of the plant.

Gels made for this purpose will also commonly contain fungicides and, or, bactericides used to maintain a sterile environment necessary to prevent the onset of harmful soil diseases such as phytophthora and pythium.

In accordance with the method of the present invention for stimulating root growth formation from a cutting, a rooting composition as described above, including a gel as described above and having an auxin in an amount effective to stimulate root growth, is adhered to the cutting. The adhering may be by any convenient technique, including dipping the cutting in the gel, adding the gel to a hole dug in soil or appropriate growing medium and inserting the cutting, or the like. The gel is generally adhered to the portion of the cutting proximal to where it was cut from a living plant. The cutting is planted with the gel still adhered thereto in soil. The term soil is used broadly to include natural soil and artificial growing media. That is, the cutting may simply be planted in the earth, or in a pot filled with earth, or can be planted in any desired soil type solid medium, by which is meant a medium in which roots can develop and which includes the essential nutrients for plant growth.

When the gel coated cutting is inserted into a hole in the soil and the soil is pressed down around it, the gel spreads out into the soil for some distance around the cutting, greatly increasing its usable surface area and extending its ability to supply water and minerals.

Since the gel is water swellable it can absorb water from the surrounding soil and act as a root would, thereby supplying nutrients from the soil to the cutting from the time of planting. Accordingly, the cutting receives considerably more water and nutrients than do cuttings which do not have such a gel adhered thereto and thereby reducing plant stress factors related to water and mineral deficiencies. Furthermore, the auxin is kept available to the cutting since it is generally hydrogen bonded to appropriate portions of the gel, making it transportable to the plant unlike prior art compositions. This serves to provide an enhanced root growth stimulating effect.

The invention will be better understood by reference to the following experimental examples.

EXAMPLE 1

Rate of Growth of Hibiscus

Cultivar: Hibiscus, Rosa-Sinensis
Duration Of Experiment: 8 weeks
Propogation Compositions Compared:
I. 0.2% NAA, 0.1% IBA adsorbed on talc
II. 0.2% NAA*, 0.1% IBA* in cross-linked polyacrylic acid gel (Carbopol 940)
Location: Oahu, Hawaii Experiment was performed on approximately 1080 cuttings. Half were treated with composition I, the remainder with composition II. The results are set forth in Table I.

TABLE I

|  | Growth Time | | | | | |
|  | 2 weeks | | 4 weeks | | 8 weeks | |
| Composition | I | II | I | II | I | II |
| --- | --- | --- | --- | --- | --- | --- |
| Callus Formation | 46% | 72% | 87% | 96% | 87% | 96% |
| Root Formation | 7% | 26% | 82% | 96% | 87% | 96% |
| Height of Plants | 2" | 2¼" | 2¼" | 3¼" | 5" | 8" |

*In lithium form. Also included nitrogen, magnesium, potassium and phosphorous nutrients.

EXAMPLE 2

Wilt Resistance

Cultivar: Dieffenbachia moculate 'camille'
Duration Of Experiment: 2 weeks
Propogation Compositions Compared: Same as in Example I
Location: Oahu, Hawaii
It is common for dieffenbachia cuttings to experience heavy wilt for the first 10 days to 2 weeks after "sticking". Samples propogated with composition II showed little to no wilt for the duration whereas those propogated with composition I showed extreme wilting for the first 6 days and gradually revived until only slight wilting was visible at the end of 2 weeks. Composition II showed only minimal signs of wilt for the first 2 to 3 days whereafter no signs of wilt were present.

EXAMPLE 3

Placement of Roots on the Stem During Propogation Cycle

Cultivar: Chrysanthemum (various)

In experiments conducted by members of the National Chrysanthemum Society, members found that callus and root formation occurred all along that portion of stem which was below soil level on cuttings propogated with composition II, whereas cuttings propogated with composition I showed callus and root formulation generalized only near the very tip of the cutting. It is believed that the lithium, which is used in medicine to increase membrane permeability, was a major contributor to callus and root formation occurring all along that portion of the stem below soil level.

The foregoing examples demonstrate the effectiveness of a composition in accordance with the present invention in promoting the rooting of cuttings.

Industrial Applicability

The present invention provides a rooting composition and method which significantly improves plant propogation via the rooting of cuttings.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A rooting composition comprising a water swellable gel containing auxin in an amount effective to stimulate root growth, said gel comprising a high molecular weight organic acid, ketone or ester or combinations thereof.

2. A rooting composition as set forth in claim 1, wherein said gel has carboxylate and/or alkoxy groups.

3. A rooting composition as set forth in claim 1, wherein said auxin is indole-3-butyric acid, 1-naphthalene-acetic acid, phenyl indole-3-butyrate, phenoxyacetic acid, phenyl indole-3-thiobutyrate, indole-propyonic acid, phenylacetic acid, indolecinnamic acid, phenylindole-3-acetate, 4-chlorophenyl indole-3-butyrate, 4-chlorophenyl indole-3-acetate, 2,4,6-tribromophenyl indole-3-butyrate, phenyl indole-3-thioloacetate, 2,4-thichlorophenyl indole-3-butyrate, 2,4,6-tribromophenyl indole-3-acetate, 4-carboxyphenyl indole-3-acetate, 4-carbethoxyphenyl indole-3-butyrate, 4-(carbomethoxyvinylene- phenyl) indole-3-acetate, 4-(carbomethoxyvinylenephenyl) indole-3-butyrate, 4-(carbomethoxyvinylene-2,6-dimethoxyphenyl) indole-3-acetate, 4-(carbomethoxyvinylene-2,6-dimethoxyphenyl) indole-3-butyrate, caulerpin salts thereof, or mixtures.

4. A rooting composition as set forth in claim 3, wherein said gel comprises a polyacrylic acid polymer, including salt forms thereof, a carboxyvinyl polymer, a pyrrolidone polymer, a gel made from diclofenac salts, a carboxyvinyl polymer, a copolymer of vinyl acetate with a polyvinyl ether, a polymer of acrylic acid, an acrylic acid ester or an acrylic acid derivative with one or more polyhydroxy compounds having at least 3 and preferably not more than 8 hydroxy groups, a sulfonated polyvinyl toluene polymer, a copolymer of acrylonitrile, a polycarboxylate hydrocarbon polymer having carboxyl groups in the form of an alkaline metal, ammonium or amine salt, or a polyacrylic acid cross-linked with a polyalkenyl polyether or combinations thereof.

5. A rooting composition as set forth in claim 1, wherein said gel comprises a polyacrylic acid polymers including salt forms thereof, a carboxyvinyl polymer, a pyrrolidone polymer, a gel made from diclofenac salts, a carboxyvinyl polymer, a copolymer of vinyl acetate with a polyvinyl ether, a polymer of acrylic acid, an acrylic acid ester or an acrylic acid derivative with one or more polyhydroxy compounds having at least 3 and preferably not more than 8 hydroxy groups, a sulfonated polyvinyl toluene polymer, a copolymer of acrylonitrile, a polycrboxylate hydrocarbon polymer having carboxyl groups in the form of an alkaline metal, ammonium or amine salt, a polyacrylic acid cross-linked with a polyalkenyl polyether or combinations thereof.

6. A rooting composition as set forth in claim 1, wherein said gel further comprises nutrients.

7. A rooting composition as set forth in claim 6, wherein said gel further comprises one or more fungicides.

8. A rooting composition as set forth in claim 7, wherein said gel further comprises one or more bactericides.

9. A rooting composition as set forth in claim 6, wherein said nutrients include one or more of nitrogen, phosphorous, potassium, calcium, magnesium, boron, chlorine, cobalt, copper, iron, manganese, molybdenum, sodium, zinc and sulfur, in . elemental or appropriate molecular forms compatible with solvation in the gel.

10. A rooting composition as set forth in claim 1, wherein said gel comprises a polyacrylic acid cross-linked with a polyalkylene polyether.

11. A rooting composition as set forth in claim 10, wherein said polyalkylene ether comprises polyallyl sucrose and/or polyallyl pentaerythritol.

12. A rooting composition as set forth in claim 1, wherein said auxin is in lithium salt form.

13. A method of stimulating root formation of a cutting, comprising:
adhering a water swellable gel containing auxin in an amount effective to stimulate root growth to the portion of the cutting proximal where it was cut from a living plant; and
planting the cutting, with the gel adhered thereto, in soil.

14. A method as set forth in claim 13, wherein said gel has carboxylate and/or alkoxy groups.

15. A method as set forth in claim 13, wherein said auxin is indole-3-butyric acid, 1-naphthalene-acetic acid, phenyl indole-3-butyrate, phenoxyacetic acid, phenyl indole-3-thiobutyrate, indole-propyonic acid, phenylacetic acid, indolecinnamic acid, phenyl-indole-3-acetate, 4-chlorophenyl indole-3-butyrate, 4-chlorophenyl indole-3-acetate, 2,4,6-tribromophenyl indole-3-butyrate, phenyl indole-3-thioloacetate, 2,4-thichlorophenyl indole-3-butyrate, 2,4,6-tribromophenyl indole-3-acetate, 4-carboxyphenyl indole-3-acetate, 4-carbethoxyphenyl indole-3-butyrate, 4-(carbomethoxyvinylene- phenyl) indole-3-acetate, 4-(carbomethoxyvinylenephenyl) indole-3-butyrate, 4-(carbomethoxyvinylene-2,6-dimethoxyphenyl) indole-3-acetate, 4-

(carbomethoxyvinylene-2,6-dimethoxyphenyl) indole-3-butyrate, and caulerpin salts thereof, or mixtures thereof.

16. A method as set forth in claim 15, wherein said gel comprises a polyacrylic acid polymer, including salt forms thereof, a carboxyvinyl polymer, a pyrrolidone polymers, a gel made from diclofenac salts, a carboxyvinyl polymer, a copolymer of vinyl acetate with a polyvinyl ether, a polymer of acrylic acid, an acrylic acid ester or an acrylic acid derivative with one or more polyhydroxy compounds having at least 3 and preferably not more than 8 hydroxy groups, sulfonated polyvinyl toluene polymer, a copolymer of acrylonitrile, a polycarboxylate hydrocarbon polymer having carboxyl groups in the form of an alkaline metal, ammonium or amine .salt, a polyacrylic acid cross-linked with a polyalkenyl polyether or combinations thereof.

17. A method as set forth in claim 13, wherein said gel comprises a polyacrylic acid polymer, including salt forms thereof, a carboxyvinyl polymer, a pyrrolidone polymers, a gel made from diclofenac salts, a carboxyvinyl polymer, copolymer of vinyl acetate with a polyvinyl ether, a polymer of acrylic acid, an acrylic acid ester or an acrylic acid derivative with one or more polyhydroxy compounds having at least 3 and preferably not more than 8 hydroxy groups, a sulfonated polyvinyl toluene polymer, a copolymer of acrylonitrile, a polycarboxylate hydrocarbon polymer having carboxyl groups in the form of an alkaline metal, ammonium or amine salt, a polyacrylic acid cross-linked with a polyalkenyl polyether or combinations thereof.

18. A method as set forth in claim 13, wherein said gel further comprises nutrients.

19. A method as set forth in claim 18, wherein said nutrients include one or more of nitrogen, phosphorous, potassium, calcium, magnesium, boron, chlorine, cobalt, copper, iron, manganese, molybdenum, sodium, zinc and sulfur in elemental or appropriate molecular forms compatible with solvation in the gel.

20. A method as set forth in claim 18, wherein said gel further comprises one or more fungicides.

21. A method as set forth in claim 20, wherein said gel further comprises one or more bactericides.

22. A method as set forth in claim 13, wherein said gel comprises a polyacrylic acid cross-linked with a polyalkylene polyether.

23. A method as set forth in claim 22, wherein said polyalkylene ether comprises polyallyl sucrose and/or polyallyl pentaerythritol.

24. A method as set forth in claim 13, wherein said auxin is in lithium salt form.

* * * * *